(12) United States Patent
Barner

(10) Patent No.: US 9,216,563 B2
(45) Date of Patent: Dec. 22, 2015

(54) LEAD ANCHOR WITH ADHESIVE AND SYSTEMS AND METHODS USING THE LEAD ANCHOR

(71) Applicant: BOSTON SCIENTIFIC NEUROMODULATION CORPORATION, Valencia, CA (US)

(72) Inventor: Paul Keith Barner, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/457,640

(22) Filed: Aug. 12, 2014

(65) Prior Publication Data

US 2015/0051675 A1 Feb. 19, 2015

Related U.S. Application Data

(60) Provisional application No. 61/867,403, filed on Aug. 19, 2013.

(51) Int. Cl.
*A61N 1/05* (2006.01)
*B32B 38/00* (2006.01)

(52) U.S. Cl.
CPC .......... *B32B 38/0008* (2013.01); *A61N 1/0558* (2013.01); *Y10T 156/1056* (2015.01)

(58) Field of Classification Search
None
See application file for complete search history.

(56) References Cited

U.S. PATENT DOCUMENTS

| 3,866,615 | A | 2/1975 | Hewson |
|---|---|---|---|
| 4,141,752 | A | 2/1979 | Shipko |
| 4,276,882 | A | 7/1981 | Dickhudt et al. |
| 4,316,471 | A | 2/1982 | Shipko et al. |
| 4,462,401 | A | 7/1984 | Burgio |
| 4,632,670 | A | 12/1986 | Mueller, Jr. |
| 4,764,132 | A | 8/1988 | Stutz, Jr. |
| 4,858,623 | A | 8/1989 | Bradshaw et al. |
| 5,036,862 | A | 8/1991 | Pohndorf |
| 5,107,856 | A | 4/1992 | Kristiansen et al. |

(Continued)

FOREIGN PATENT DOCUMENTS

| EP | 85417 A1 | 8/1983 |
|---|---|---|
| EP | 0597213 A1 | 5/1994 |

(Continued)

OTHER PUBLICATIONS

U.S. Appl. No. 14/457,602, filed Aug. 12, 2014.

(Continued)

*Primary Examiner* — Erica Lee
(74) *Attorney, Agent, or Firm* — Lowe Graham Jones PLLC; Bruce E. Black

(57) ABSTRACT

A lead anchor includes an anchor body having an outer surface, a top end, a front side, a first end, and a second end disposed opposite to the first end. The anchor body defines a longitudinal lead lumen extending from the first end of the anchor body to the second end of the anchor body. The lead lumen is configured and arranged to receive a portion of a lead. A transverse lumen extends from the top end of the anchor body and perpendicularly intersects the lead lumen. An adhesive is disposed within a shell. The adhesive and shell are disposed in the transverse lumen of the anchor body and are configured and arranged for fastening the received lead to the lead anchor by piercing the shell to release the adhesive so that the adhesive passes through the transverse lumen into the lead lumen and into contact with the received lead.

20 Claims, 8 Drawing Sheets

(56) References Cited

U.S. PATENT DOCUMENTS

| | | |
|---|---|---|
| 5,158,097 A | 10/1992 | Christlieb |
| 5,228,248 A | 7/1993 | Haddock |
| 5,376,108 A | 12/1994 | Collins et al. |
| 5,484,445 A | 1/1996 | Knuth |
| 5,865,843 A | 2/1999 | Baudino |
| 5,957,968 A | 9/1999 | Belden et al. |
| 6,181,969 B1 | 1/2001 | Gord |
| 6,192,279 B1 | 2/2001 | Barreras, Sr. et al. |
| 6,360,750 B1 | 3/2002 | Gerber et al. |
| 6,473,654 B1 | 10/2002 | Chinn |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,894,145 B2 | 5/2005 | Xiao et al. |
| 6,901,287 B2 | 5/2005 | Davis et al. |
| 6,978,180 B2 | 12/2005 | Tadlock |
| 7,069,083 B2 | 6/2006 | Finch et al. |
| 7,072,719 B2 | 7/2006 | Vinup et al. |
| 7,161,461 B1 | 1/2007 | Nelson |
| 7,244,150 B1 | 7/2007 | Brase et al. |
| 7,343,202 B2 | 3/2008 | Mrva et al. |
| 7,437,193 B2 | 10/2008 | Parramon et al. |
| 7,447,546 B2 | 11/2008 | Kim et al. |
| 7,672,734 B2 | 3/2010 | Anderson et al. |
| 7,761,165 B1 | 7/2010 | He et al. |
| 7,787,960 B2 | 8/2010 | Lubenow |
| 7,848,803 B1 | 12/2010 | Jaax et al. |
| 7,853,321 B2 | 12/2010 | Jaax et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,224,451 B2 | 7/2012 | Jaax et al. |
| 8,229,573 B2 | 7/2012 | Chen et al. |
| 8,315,704 B2 | 11/2012 | Jaax et al. |
| 8,364,278 B2 | 1/2013 | Pianca et al. |
| 2001/0000187 A1 | 4/2001 | Peckham et al. |
| 2002/0107554 A1 | 8/2002 | Biggs et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0206162 A1 | 9/2006 | Wahlstrand et al. |
| 2007/0050005 A1 | 3/2007 | Lauro |
| 2007/0078399 A1 | 4/2007 | Olson |
| 2007/0150036 A1 | 6/2007 | Anderson |
| 2007/0219595 A1 | 9/2007 | He |
| 2007/0255369 A1 | 11/2007 | Bonde et al. |
| 2008/0071320 A1 | 3/2008 | Brase |
| 2008/0091255 A1 | 4/2008 | Caparso et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0228251 A1 | 9/2008 | Hill |
| 2008/0243220 A1 | 10/2008 | Barker |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0198312 A1* | 8/2009 | Barker .......... 607/116 |
| 2009/0254151 A1 | 10/2009 | Anderson et al. |
| 2009/0270940 A1 | 10/2009 | Deininger |
| 2010/0174240 A1* | 7/2010 | Wells et al. .......... 604/175 |
| 2010/0274336 A1 | 10/2010 | Nguyen-Stella et al. |
| 2010/0312319 A1 | 12/2010 | Barker |
| 2011/0022142 A1 | 1/2011 | Barker et al. |
| 2011/0060395 A1 | 3/2011 | Cantlon |
| 2011/0178573 A1 | 7/2011 | Nguyen-Stella et al. |
| 2012/0150202 A1 | 6/2012 | Chen et al. |
| 2012/0185027 A1 | 7/2012 | Pianca et al. |
| 2012/0232626 A1 | 9/2012 | Daglow |
| 2012/0277670 A1 | 11/2012 | Goetz |
| 2012/0330355 A1 | 12/2012 | Finley et al. |
| 2013/0204336 A1 | 8/2013 | Sharma |

FOREIGN PATENT DOCUMENTS

| | | |
|---|---|---|
| WO | 9833551 A1 | 8/1998 |
| WO | 99/53994 | 10/1999 |
| WO | 00/13743 A2 | 3/2000 |
| WO | 00/64535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2013112920 A1 | 8/2013 |

OTHER PUBLICATIONS

U.S. Appl. No. 14/452,467, filed Aug. 5, 2014.
U.S. Appl. No. 14/312,194, filed Jun. 23, 2014.

* cited by examiner

LEAD ANCHOR WITH ADHESIVE AND SYSTEMS AND METHODS USING THE LEAD ANCHOR

CROSS-REFERENCE TO RELATED APPLICATIONS

This application claims the benefit under 35 U.S.C. §119 (e) of U.S. Provisional Patent Application Ser. No. 61/867,403, filed Aug. 19, 2013, which is incorporated herein by reference.

FIELD

The present invention is directed to the area of implantable electrical stimulation systems and methods of making and using the systems. The present invention is also directed to lead anchors using adhesive for holding the lead, as well as methods of making and using the lead anchors with leads and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue. A lead anchor is often used to anchor the lead and hold the lead in a desired position with respect to tissue of the patient.

BRIEF SUMMARY

One embodiment is a lead anchor that includes an anchor body having an outer surface, a top end, a first end, and a second end that is opposite to the first end. The anchor body defines a longitudinal lumen and a transverse lumen. The longitudinal lumen extends from the first end of the anchor body to the second end of the anchor body and is configured and arranged to receive a portion of a lead. The transverse lumen extends from the top end of the anchor body and perpendicularly intersects the lead lumen. The anchor body also includes a shell and adhesive disposed within the shell. The shell and adhesive are disposed in the transverse lumen of the anchor body and are configured and arranged for fastening the received lead to the lead anchor by piercing the shell to release the adhesive so that the adhesive passes through the transverse lumen into the lead lumen and into contact with the received lead.

A further embodiment is a kit including an implantable stimulation lead and the lead anchor described above. The lead anchor is configured and arranged to receive a portion of the implantable stimulation lead within the connector of the lead extension.

Another embodiment is a lead extension including an extension body having a proximal portion, a distal end, and a longitudinal length. Multiple terminals are disposed along the proximal portion of the extension body. A connector is disposed on the distal end of the extension body. The connector has a proximal end, a distal end, a top end, and a longitudinal length. The connector is configured and arranged to receive a proximal portion of an electrical stimulation lead. The connector includes a connector housing defining a port open at the distal end of the connector. The port is configured and arranged for receiving the proximal end of the electrical stimulation lead. Multiple connector contacts are disposed in the connector housing and are configured and arranged to couple to at least one of the multiple terminals disposed on the proximal end of the electrical stimulation lead. A transverse lumen extends from the top end of the connector and perpendicularly intersects the port. The connector further includes a shell and an adhesive disposed within the shell. The shell and the adhesive are disposed in the transverse lumen and are configured and arranged for fastening the received lead to the lead extension by piercing the shell to release the adhesive so that the adhesive passes through the transverse lumen into the port and into contact with the received lead.

Another embodiment is a kit including an implantable stimulation lead and the lead extension described above. The lead extension is configured and arranged to receive a portion of the implantable stimulation lead within the connector of the lead extension.

Yet another embodiment is a method of attaching a lead anchor to an electrical stimulation lead. The method includes inserting a portion of the electrical stimulation lead into the lead lumen of the lead anchor described above. The shell is pierced within the lead anchor to release the adhesive. The adhesive is allowed to enter the lead lumen to make contact with the lead and the adhesive is then cured for attaching the lead anchor to the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to lead anchors using adhesive for holding the lead, as well as methods of making and using the lead anchors with leads and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; 7,761,165; 7,974,706; 8,175,710; 8,224,450; and 8,364,278; and U.S. Patent Application Publication No. 2007/0150036, all of which are incorporated by reference.

Figure 1:
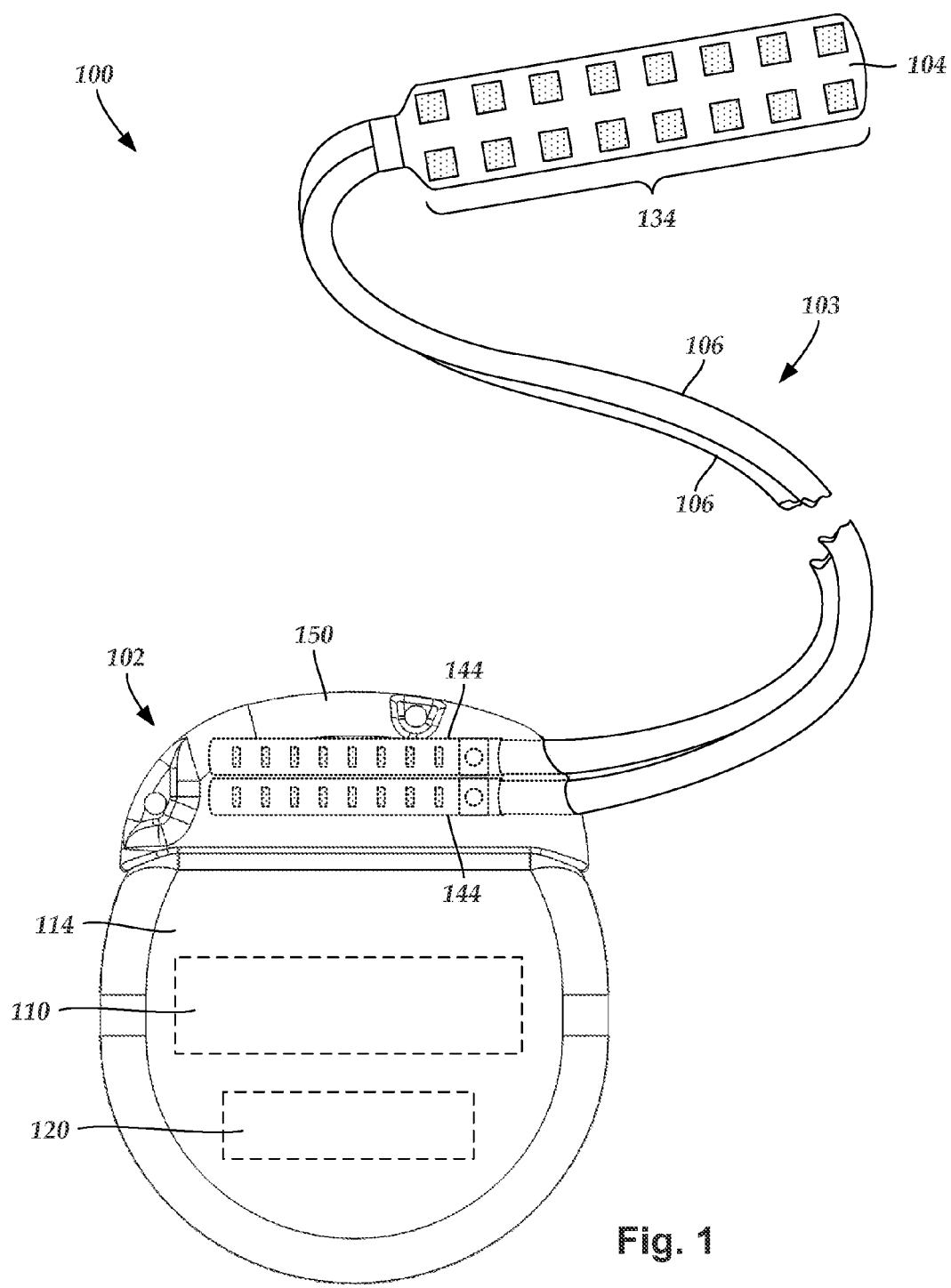
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
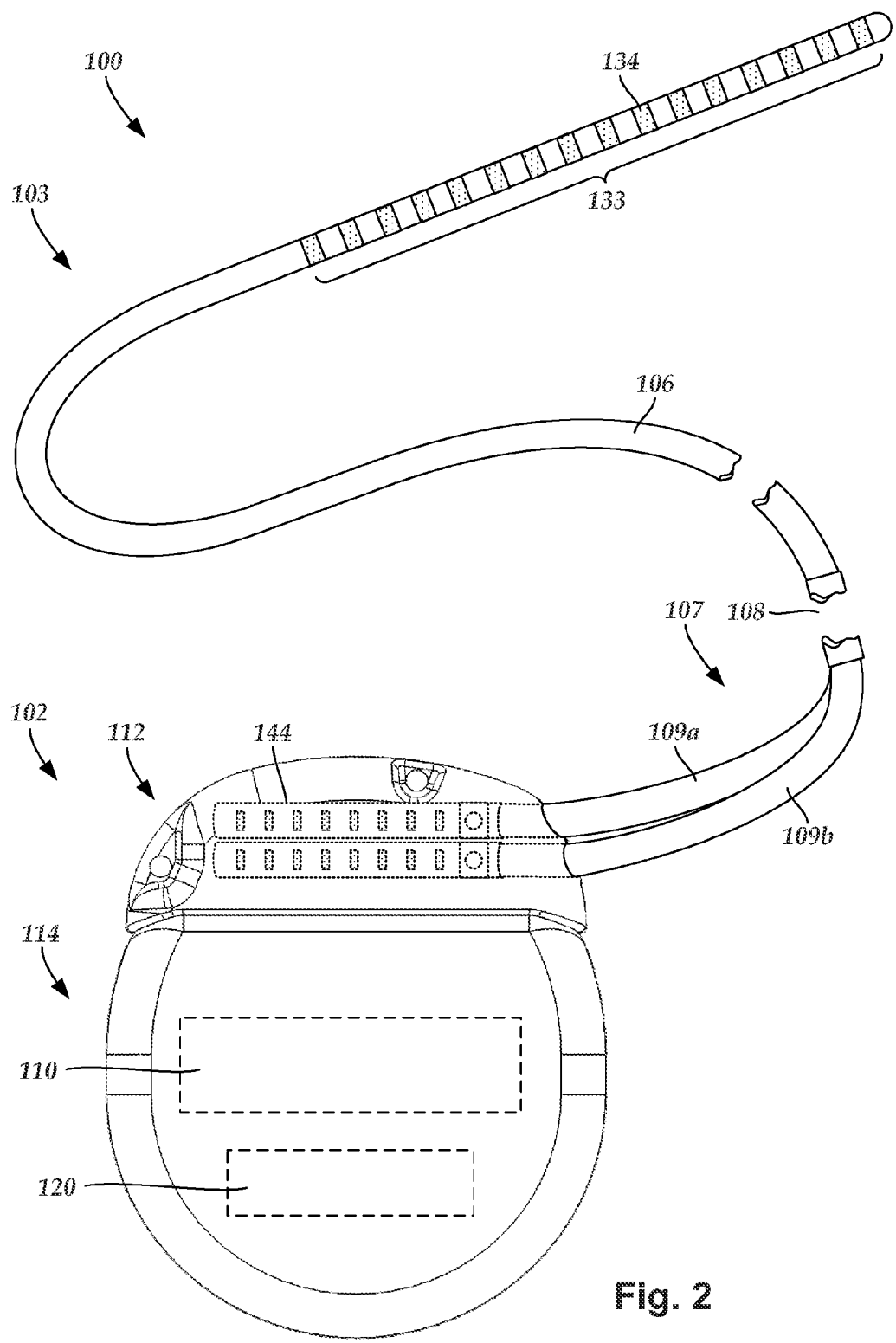
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
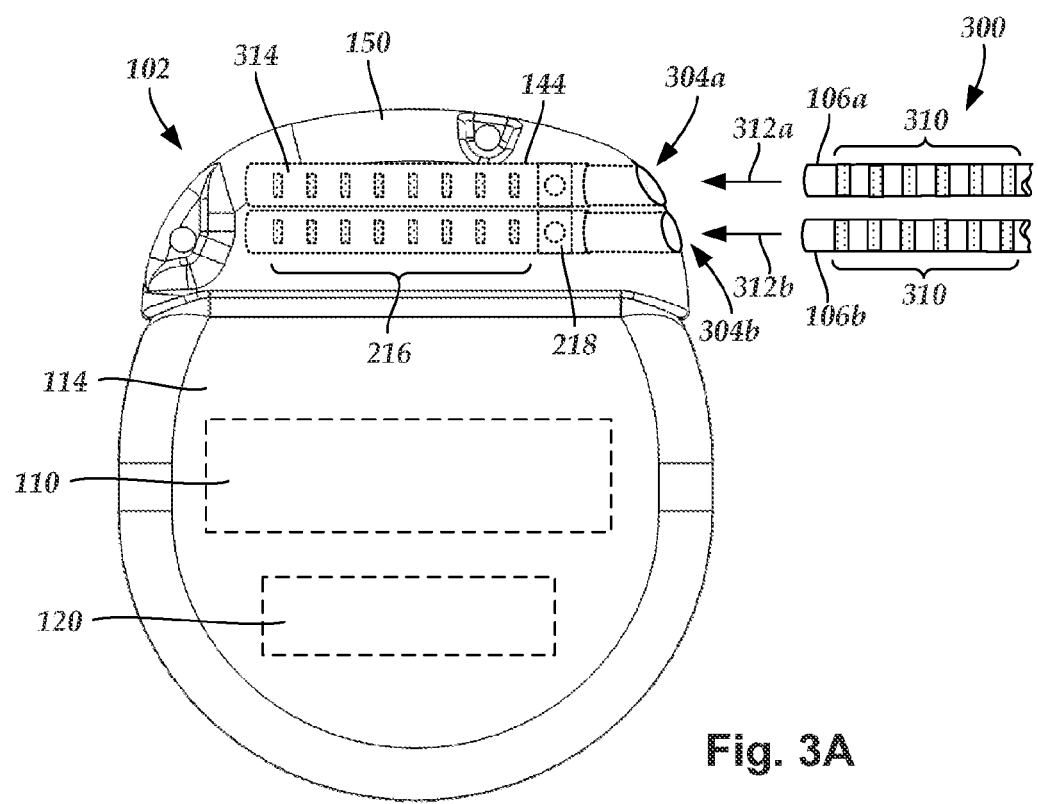
FIG. 3A is a schematic view of one embodiment of the control module of FIG. 1 configured and arranged to electrically couple to an elongated device, according to the invention.
Figure 3B:
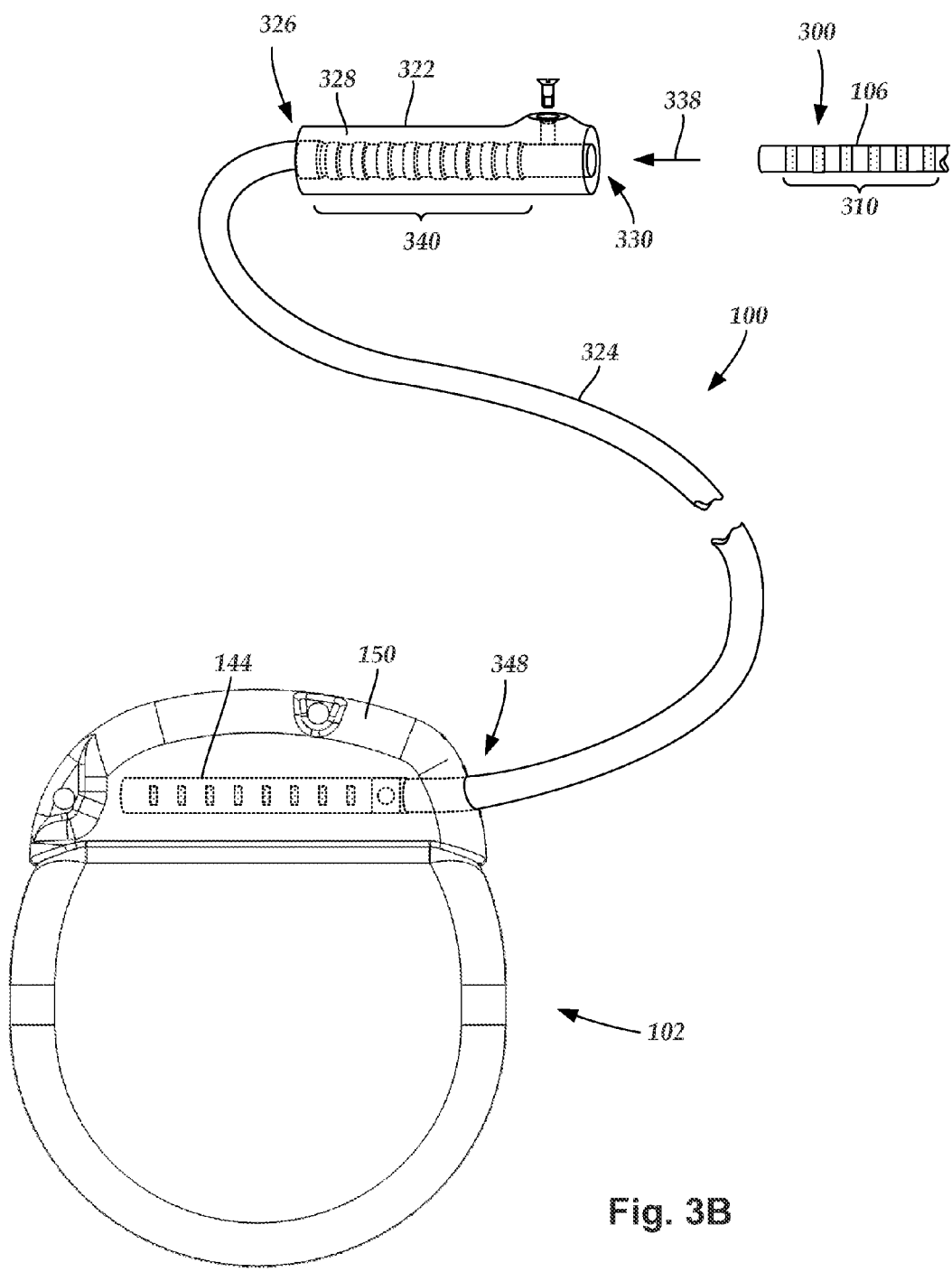
FIG. 3B is a schematic view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 240 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

A lead anchor can be used in an implantable device, such as an implantable spinal cord stimulator, to anchor a lead connecting a control module to an electrode array. Many conventional lead anchors use a set-screw to hold a lead within the lead anchor by applying a holding force on the lead. However, such a force applied beyond a limit can cause damage to the lead. On the other hand, if the force applied is to low, there may be lead migration. In contrast, the lead anchor describe herein uses a pre-loaded adhesive "bubble" to apply adhesive, by bursting the "bubble" to hold the lead within the lead anchor.

Figure 4A:
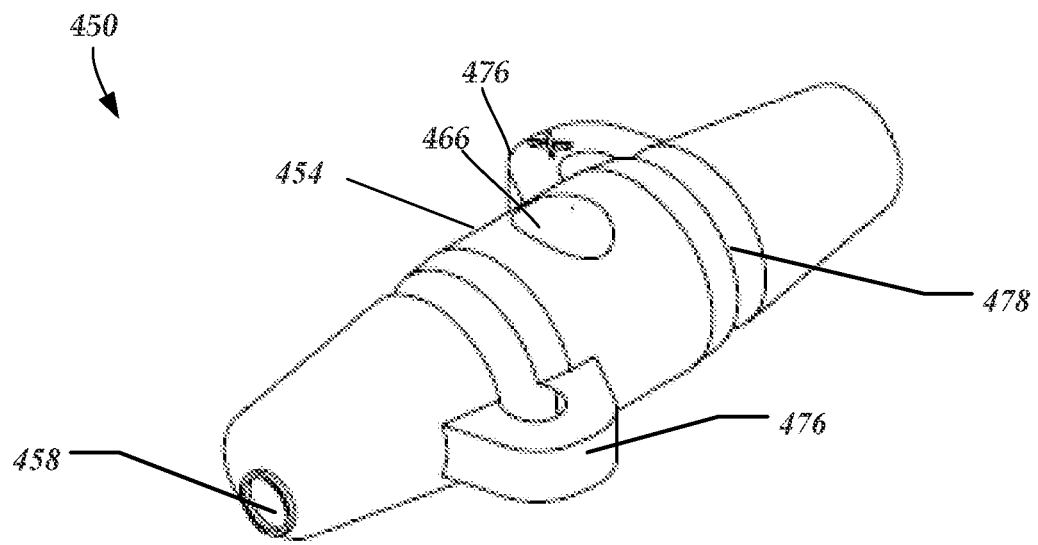
FIG. 4A is a schematic top perspective view of one embodiment of a lead anchor, according to the invention.
Figure 4B:
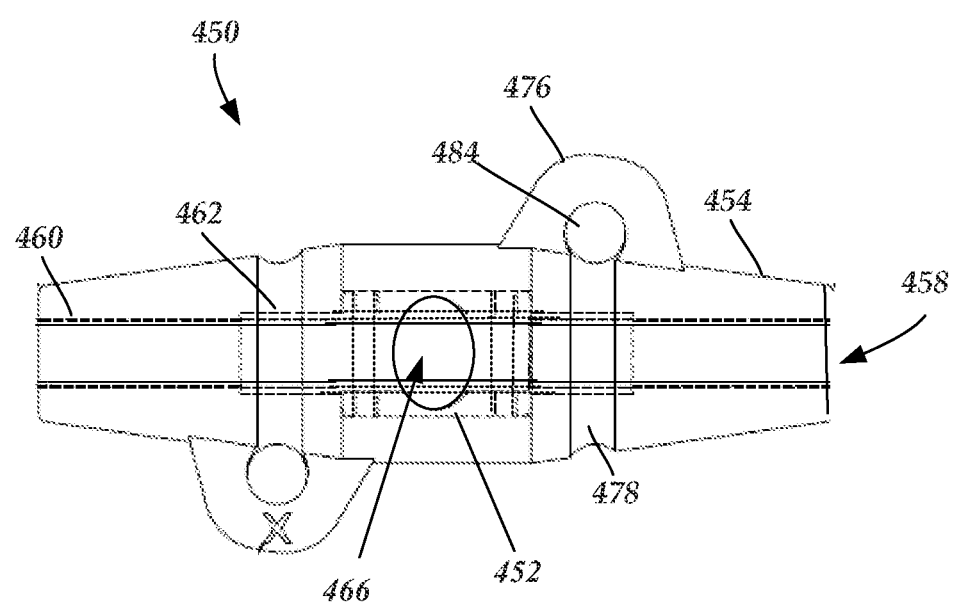
FIG. 4B is a schematic top view of the lead anchor of FIG. 4A, according to the invention.

FIG. 4A illustrates one embodiment of a lead anchor 450 that includes an exterior member 454 disposed around an anchor body 452 (see, FIG. 4B). The exterior member 454 can be made of any suitable biocompatible material, for example, a plastic or polymer, such as, silicone, polyvinylchloride, polyurethane, or the like; a biocompatible metal or alloy, such as titanium or titanium alloys, nickel, aluminum, stainless steel, gold, silver, platinum or alloys thereof, or any other suitable biocompatible material or combination of materials. In at least some embodiments, the exterior member 454 is made of silicone. The exterior member 454 may partially or completely surround the anchor body. In some embodiments, the exterior member 454 forms a pliable or flexible skin around the anchor body 452.

Furthermore, it may be useful for any or all parts of the lead anchor 450 to be made of, or incorporate, a radiopaque material, so that it is visible using fluoroscopy or other forms of X-ray imaging.

In some embodiments, the exterior member 454 has a shape that is substantially oblong. It will be recognized, however that other shapes may also be suitable for the exterior member 454 including rectangular, cylindrical, elliptical, or any other regular or irregular shape, or the like.

In some embodiments, the exterior member 454 is shaped such that its diameter increases as it extends longitudinally from one point to another point along its length. In some other embodiments, the exterior member 454 has a variable diameter that increases from one end to the middle, and then decreases from the middle to the opposite end.

The exterior member 454 optionally defines at least one suture groove 478. The suture groove 478 can be a depression in the outer surface of the exterior member 454, and may be circumferentially (or partially circumferentially) disposed at any location around the exterior member 454. The suture groove 478 is dimensioned to receive a suture. In some embodiments, a number of suture grooves 478 are defined in the exterior member 454.

Any number of tabs, such as a tab 476 (also shown in FIG. 4B) can be attached at or adjacent to the suture grooves 478, and may extend radially outward from the exterior surface of the lead anchor. The tab 476 is provided to secure the lead anchor with patient tissue. In some embodiments, the tab 476 and the exterior member 454 are made of the same material. In some embodiments, the tab 476 and the exterior member 454 are unitary. The tab 476 can have a substantially semi-circular cross-section. It will be recognized, however, that other shapes are also suitable including rectangular, square, elliptical, or the like.

As shown in FIG. 4A, an aperture 466 is an opening defined on the exterior member 454 such that a lumen in the anchor body and transverse to the longitudinal body of the exterior member 454 can be accessed. Further, a lead lumen 458 is provided, at least in part, as a channel defined by the anchor body (shown in FIG. 4B). The lead lumen 458 extends along a longitudinal length of the exterior member 454. The lead lumen 458 may be dimensioned to receive the lead proximally or distally, and to form a friction fit with the lead. In some embodiments, the lead lumen 458 may include interior threads, ridges, micro patterns, or another suitable roughening of its surface to facilitate or enhance engagement with a lead.

The lead lumen 458 may have a substantially circular cross-section along the longitudinal length of the exterior member 454. However, the lead lumen 458 may also have any other cross-sectional shape that is reasonably sufficient to house the lead, including but not limited to the following shapes: triangle, square, ovoid, or the like.

FIG. 4B is a schematic top view of the lead anchor 450 of FIG. 4A. The lead anchor 450 includes the anchor body 452. The anchor body 452 may be made of a biocompatible metal, such as titanium, nickel, aluminum, stainless steel, copper, gold, silver, platinum and alloys, or the like, or a rigid plastic or polymer material like polyetheretherketone, polyvinylchloride, polytetrafluoroethylene, or the like. In some embodiments, the anchor body 452 is made from the same material as that of the exterior member 454. In some embodiments, the anchor body 452 and the exterior member 454 are unitary.

The anchor body 452 can have a cross-section that is substantially rectangular. It will be recognized, however, that other shapes are also suitable including square, cylindrical, oblong, elliptical, or the like.

In at least some embodiments, the anchor body 452 is disposed in a cavity within the exterior member 454. For example, the anchor body 452 can be disposed within the largest portion of the exterior member 454, i.e., the portion of the exterior member 454 that defines the largest diameter.

The anchor body 452 defines at least a portion of the lead lumen 458 through which a lead may pass. The lead lumen 458 defines two open ends on its either side for insertion of the lead.

In some embodiments, the lead lumen 458 is shaped and disposed to enable the lead to pass along a straight path through the center of the anchor body 452. In some embodiments, the lead lumen 458 may be defined so that the lead passes at an angled path through the anchor body 452. The lead lumen 458 may also be defined as a curved path through the anchor body 452. The anchor body 452 may contain more than one lead lumen, so that the lead anchor 450 is able to house more than one lead.

The lead lumen 458 can be formed by any suitable method, such as molding, piercing, boring, reaming, tapping, or the like. In some embodiments, the lead lumen 458 may include interior threads, ridges, micro patterns, or another suitable roughening of the surface of the lead lumen 458 to facilitate or enhance engagement with the lead.

In some embodiments, a lead tube 460 is disposed within and along a longitudinal axis of the anchor body 452 to secure and align the lead with respect to the lead anchor 450. The lead tube 460 can define the lead lumen 458. The lead tube 460 has an inner diameter that is sufficient to house the lead. In some embodiments, a space (or a substantial space) is defined between the lead tube 460 and the lead, which enables an adhesive to settle therein. In some embodiments, the lead tube 460 may include interior threads, ridges, micro patterns, or another suitable roughening of the surface of the lead tube 460 to facilitate or enhance engagement with the lead.

In some embodiments, a sleeve 462 is disposed over a portion of the lead tube 460. In some embodiments, the sleeve 462 is positioned beneath the aperture 466 and extends along a longitudinal axis or central axis of the anchor body 452 along the lead lumen 458. The sleeve 462 can be made of the same material as the lead tube 460, and can have the same cross-section as the lead tube 460. The sleeve 462 can have a length that is sufficient to cover a portion of the lead tube 460 and the lead. Also, the sleeve 462 and the lead tube 460 have an aperture defined below the aperture 466.

The tab 476 can include an opening 484. The suture can traverse the opening 484 as the suture travels along the suture groove 478. The opening 484 shown in FIG. 4B has a substantially circular cross-section. It will be recognized, however, that other shapes can be used for the cross-section including elliptical, oblong, rectangular, square, or the like. The opening 484 can be formed by any suitable method such as by molding, piercing, boring, reaming, tapping, or the like. A suture can be used to attach the lead anchor 450 to the fascia, ligament or other tissue or body structure.

Figure 5A:
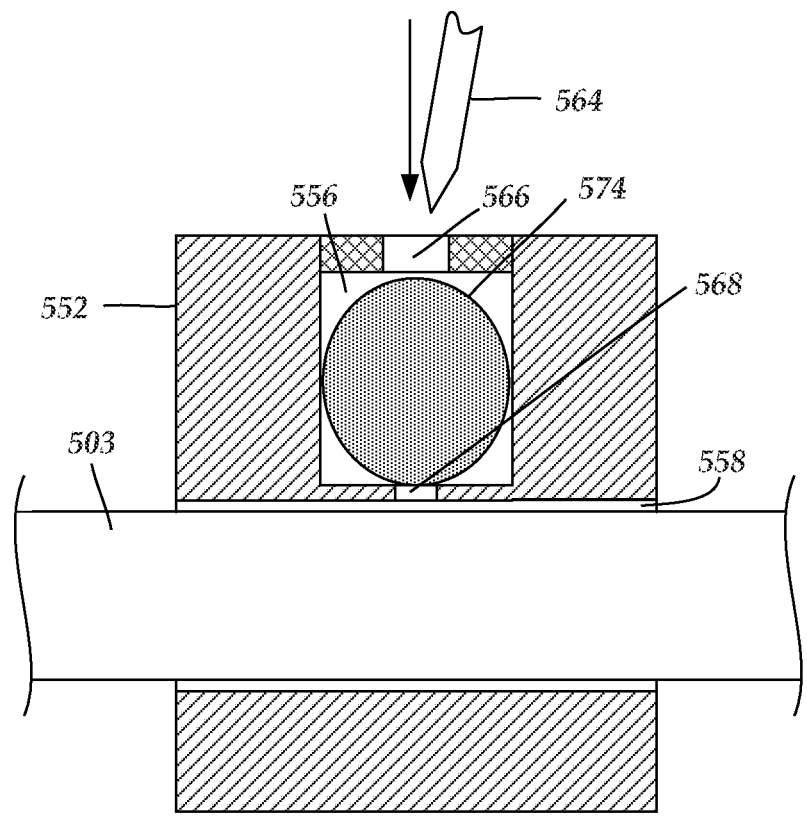
FIG. 5A is a schematic cross-sectional view of one embodiment of an anchor body of a lead anchor and associated structures, according to the invention.

FIG. 5A illustrates one embodiment of an anchor body 552 of a lead anchor. The anchor body 552 defines a longitudinal lead lumen 558 and a transverse lumen 556. The longitudinal lead lumen 558 is similar to the longitudinal lead lumen 458 of FIG. 4A. The transverse lumen 556 may have a substantially circular cross-section. In other embodiments, the anchor body 552 defines a transverse lumen 556 having cross-sectional shapes such as but are not limited to circular, elliptical, ovoid, or the like. In some embodiments, the transverse lumen 556 is relatively larger in size than the aperture 566.

The transverse lumen 556 extends from an aperture 566 at or on one end (referred to as a "top end") of the anchor body 552 and is positioned perpendicular to a longitudinal axis or central axis of the lead lumen 558. An opening 568 is defined between the transverse lumen 556 and the lead lumen 558. In at least some embodiments, the transverse lumen 556 merges with the lead lumen 558, but does not extend through it so that the cross-section of the anchor body 552 defines a t-shaped bore. In some embodiments, the transverse lumen 556 extends through the lead lumen 558 to form a cross shape.

An adhesive is disposed within the transverse lumen 556 within a shell 574. Any biocompatible adhesive can be used, including but not limited to epoxy resins, acrylic resins, polyurethane adhesives, colloidal epoxy silica, or the like. Any form of adhesive can be used, including but not limited to viscous, liquid, slurry, or the like. The adhesive may occupy or form into any shape once it is disposed in the transverse lumen 556. Examples of such shapes may include but are not limited to rectangular, spherical, square, or the like. In at least some embodiments, the shape of the adhesive depends upon the shape of the transverse lumen 556.

The shell 574 can be pliable or flexible or may be brittle. In at least some embodiments, an outer surface of the adhesive is partially cured to form the shell 574. The method of curing depends on the adhesive and may include, but is not limited to, exposure to ultraviolet (or other curing) light, exposure to heat, solvent removal, or the like. The shell 574 may form a non-adhesive, solid plastic material. In at least some embodiments, the solid shell contains the adhesive 574 in a fluid or semi-fluid state. In some other embodiments, a thin-walled shell is pre-formed and the adhesive is injected or otherwise introduced into the thin-walled shell.

In at least some embodiments, the shell 574 with adhesive is first formed and then disposed in the transverse lumen 556. The shell and adhesive may be introduced through the aperture 566. In other embodiments, the shell may be introduced into an open transverse lumen 566 and then a cap with aperture 566 inserted into the opening of the transverse lumen. Hence, the transverse lumen 556 is dimensioned to house the shell 574 and adhesive.

When the user desires to lock a lead within the anchor, a tool 564 can be advanced through the aperture 566 and the transverse lumen 556 towards the shell 574. The tool 564 can be any element that is sharp enough to pierce the shell 574. In at least some embodiments, the tool 564 has a pointed end. Examples of the tool 564 may include, but are not limited to, a pin, nail, needle, punch, or the like.

Figure 5B:
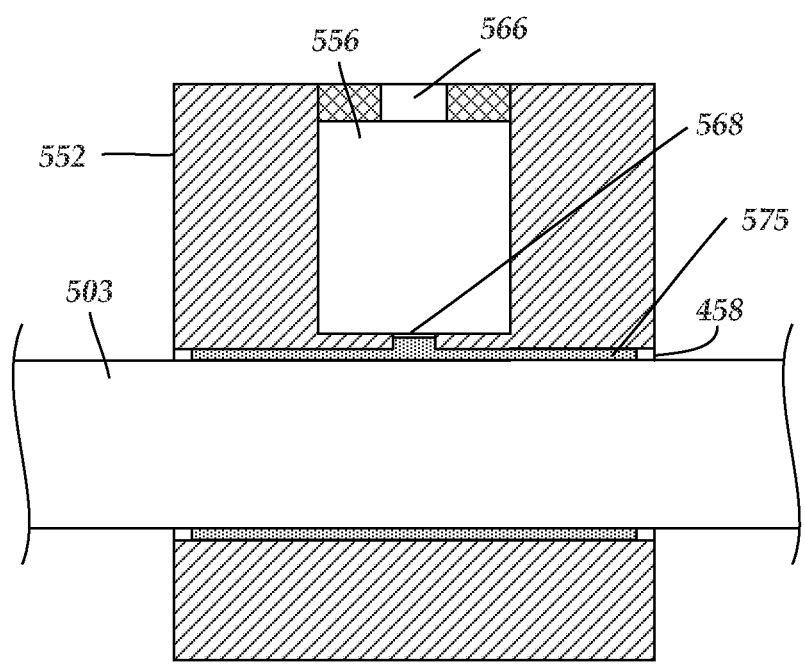
FIG. 5B is a schematic cross-sectional view of the anchor body of FIG. 5A after the shell has been pierced and the adhesive allowed to enter the lead lumen, according to the invention.

The tool 564 pierces or punctures the shell 574 to release the adhesive which passes through the transverse lumen 556 and the opening 568 into the lead lumen 558, as shown in FIG. 5B. The adhesive 575 contacts the lead 503 received in the lead lumen 558 and the adhesive 575 spreads around the lead 503. The lead 503 is attached to the lead anchor 450 via the adhesive 575. After releasing the adhesive into the lead lumen, the adhesive may be cured. The method of curing will depend on the adhesive and may include exposure to ultraviolet (or other curing) light, exposure to heat, solvent removal, or the like. In some embodiments, curing may occur without any intervention by a user, but may result from the passage of time or the exposure to body heat or by any other suitable mechanism.

Figure 6:
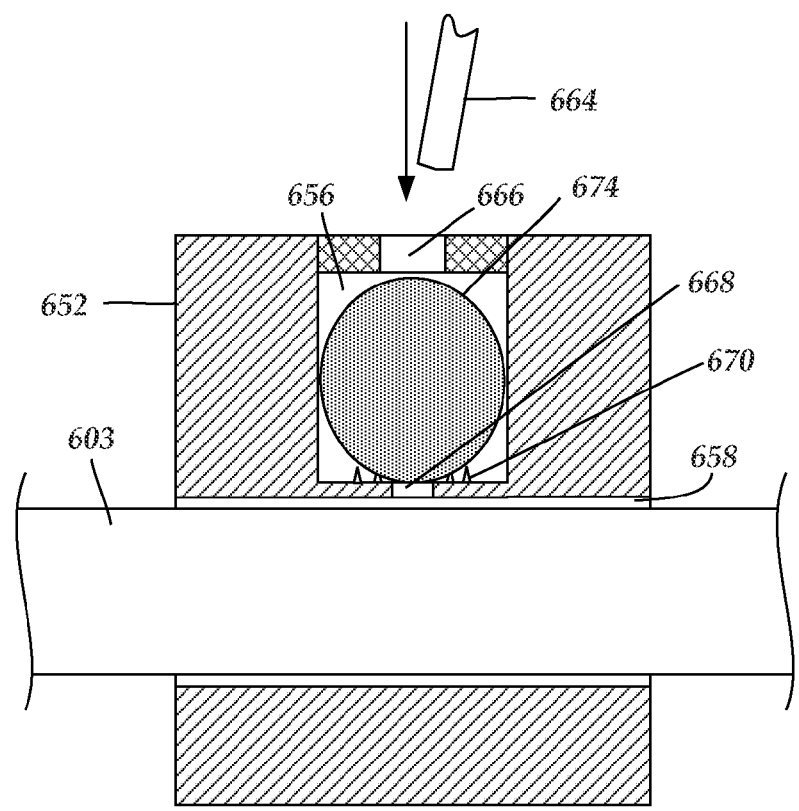
FIG. 6 is a schematic cross-sectional view of another embodiment of an anchor body of a lead anchor and associated structures, according to the invention.

FIG. 6 is a cross-sectional view of another embodiment of an anchor body of a lead anchor. The anchor body 652 defines a longitudinal lead lumen 658, and a transverse lumen 656 disposed perpendicular to the lead lumen 658. The transverse lumen 656 extends from an aperture 666 to an aperture 668 leading to the lead lumen 658. An adhesive is contained in a shell 674 that is disposed in the transverse lumen 656. Except as described below, the design and other considerations described for the anchor body 552 also apply to the anchor body 652.

Although the structure of the anchor body 652 is similar to that of the anchor body 552 of FIG. 5A, a piercing element 670 may be disposed at any location within the transverse lumen 656 such that the piercing element 670 is able to interact with the shell 674 upon receiving an external stimulus such as a tool 664. In some embodiments, the piercing element 670 protrudes from a bottom surface of the transverse lumen 656. In some embodiments, the piercing element 670 and the anchor body 652 are integral or unitary. In other embodiments, the piercing element 670 may be attached to the anchor body 652.

The piercing element 670 has pointed tip pointing towards a surface of the shell. In at least some embodiments, more than one piercing element 670 is disposed within the transverse lumen 656. The piercing elements 670 may be arranged in any arrangement such as spiral, matrix, or the like. In some embodiments, at least one piercing element 670 is disposed on each of the walls of the transverse lumen 656 and pointing towards the shell.

The tool 664 is advanced towards the shell 674 through the aperture 666 and the transverse lumen 656 such that a tip of the tool 664 pushes the shell 674 towards the pointed ends of the piercing element 670. The tool 664 may be any tool that can be inserted into the transverse lumen 656 and can thereby push the shell. Examples of such tools may include pestle, rod, pin, punch, or the like.

In at least some embodiments, a partial upper portion of the shell 674 is broken by the tool 664 and a remaining lower portion of the shell 674 is punctured by the piercing element 670 upon being engaged by the tool 664. The adhesive is released, enters into a lead lumen 658, and contacts the received lead 603.

Figure 7:
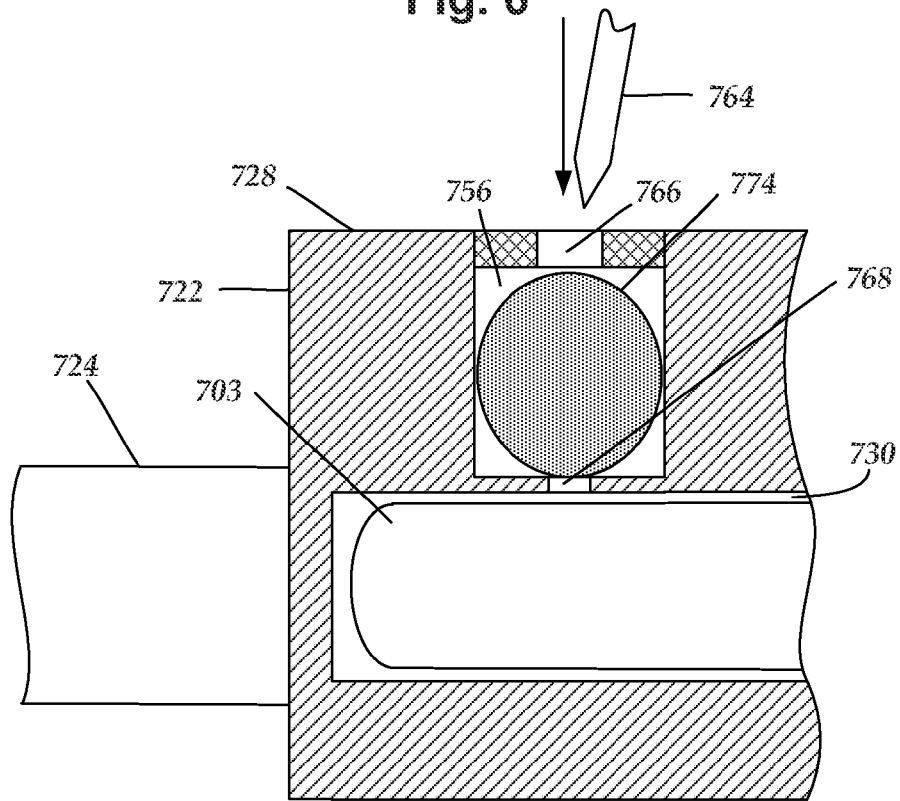
FIG. 7 is a schematic cross-sectional view of one embodiment of a portion of a lead extension and a portion of its connector, according to the invention.

FIG. 7 is a cross-sectional view of another embodiment of a portion of a lead extension and a portion of its connector. Except described below, the design and other considerations described for the lead extension 324, the connector 322, the housing 328, and the port 330 of FIG. 3B also apply to lead extension 724, connector 722, housing 728, and port 730, respectively.

Although the structure of the connector 722 is similar to that of the connector 322 of FIG. 3B, an aperture 766 is disposed on a top end of the housing 728 of the connector 722 that further extends through the housing 728 to form a transverse lumen 756. The transverse lumen 756 perpendicularly intersects the port 730.

A shell 774 with adhesive is disposed in the transverse lumen 756. The transverse, lumen, shell, and adhesive are the same as those that have been described above with respect to FIGS. 5 and 6.

A tool 764 is advanced through the aperture 766 to pierce the shell 774. In some embodiments, a piercing element is disposed in the transverse lumen 756. The adhesive flows down through the opening 768 into the port 730 and around the proximal end of the lead 703 as shown in FIG. 7. The released adhesive contacts the received lead, thereby affixing the lead 703 within the connector 722.

A method of attaching a lead anchor to an electrical stimulation lead includes a number of consecutive, non-consecutive, simultaneous, non-simultaneous, or alternative steps. For instance, the method includes inserting a portion of the electrical stimulation lead into the lead lumen of the lead anchor. A tool is inserted into an opening in the lead anchor to pierce the shell within the transverse lumen of the lead anchor. The adhesive contained in the shell is released and allowed to enter the lead lumen. The adhesive engages a portion of the lead to affix the lead to the lead anchor.

Figure 8:
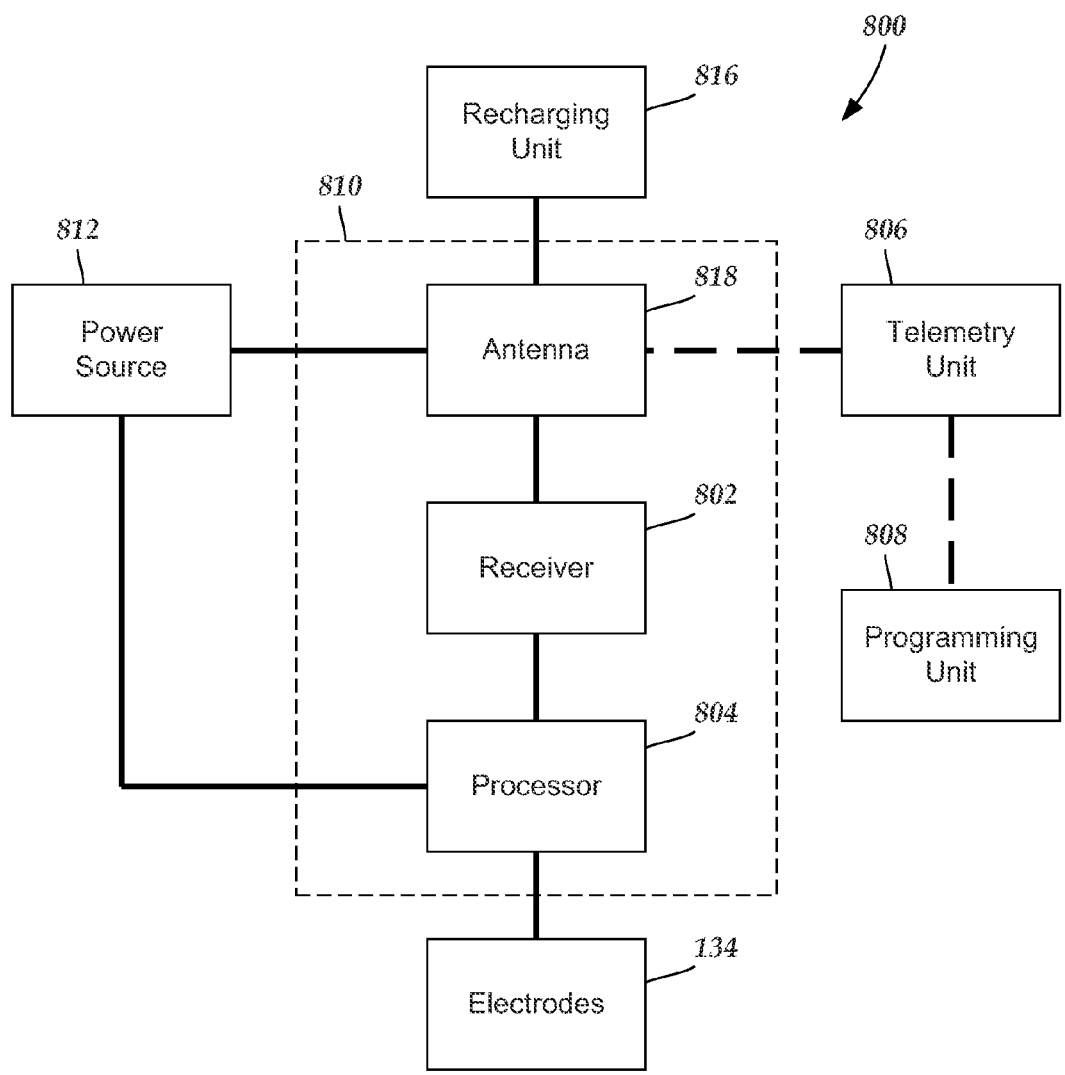
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, a power source 812, an antenna 818, a receiver 802, and a processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 selects which electrode(s) are cathodes and which electrode(s) are anodes. In some embodiments, the processor 804 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by the programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and the receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include the antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor comprising:
   an anchor body having an outer surface, a first end, and a second end opposite to the first end, the anchor body defining
      a longitudinal lead lumen extending from the first end of the anchor body to the second end of the anchor body and configured and arranged to receive a portion of a lead, and
      a transverse lumen extending from the outer surface of the anchor body and perpendicularly intersecting the lead lumen;
   a shell; and
   adhesive disposed within the shell, wherein the shell and adhesive are disposed in the transverse lumen of the anchor body and are configured and arranged for fastening the received lead to the lead anchor by piercing the shell to release the adhesive so that the adhesive passes through the transverse lumen into the lead lumen and into contact with the received lead.

2. The lead anchor of claim 1, further comprising at least one piercing element disposed in the transverse lumen and configured and arranged to pierce the shell when the shell is directed against the at least one piercing element.

3. The lead anchor of claim 1, wherein the shell is formed of a same material as the adhesive, wherein the material of the shell is at least partially cured to form the shell.

4. The lead anchor of claim 1, wherein the shell is formed of a non-adhesive, solid plastic material.

5. The lead anchor of claim 1, wherein the adhesive is an ultraviolet-curable adhesive.

6. The lead anchor of claim 1, wherein the adhesive is a heat-curable adhesive.

7. The lead anchor of claim 1, further comprising at least one tab extending from the lead anchor to attach the lead anchor to patient tissue, wherein the at least one tab extends perpendicular to the transverse lumen.

8. A kit, comprising:
an implantable stimulation lead; and
the lead anchor of claim 1 configured and arranged to receive a portion of the implantable stimulation lead within the lead lumen of the lead anchor.

9. The kit of claim 8, further comprising a tool configured and arranged so that a tip of the tool is insertable into the transverse lumen to facilitate piercing the shell within the lead anchor and releasing the adhesive.

10. A lead extension, comprising
an extension body having a proximal portion, a distal end, and a longitudinal length;
a plurality of terminals disposed along the proximal portion of the extension body; and
a connector disposed on the distal end of the extension body, the connector having a proximal end, a distal end, an outer surface, and a longitudinal length, the connector being configured and arranged to receive a proximal portion of an electrical stimulation lead, the connector comprising
a connector housing defining a port open at the distal end of the connector, the port configured and arranged for receiving the proximal portion of the electrical stimulation lead,
a plurality of connector contacts disposed in the connector housing, the plurality of connector contacts configured and arranged to couple to at least one of a plurality of terminals disposed on the proximal portion of the electrical stimulation lead,
a transverse lumen extending from the outer surface of the connector and perpendicularly intersecting the port,
a shell, and
adhesive disposed within the shell, wherein the shell and adhesive are disposed in the transverse lumen and are configured and arranged for fastening the received lead to the lead extension by piercing the shell to release the adhesive so that the adhesive passes through the transverse lumen into the port and into contact with the received lead.

11. The lead extension of claim 10, further comprising at least one piercing element disposed in the transverse lumen and configured and arranged to pierce the shell when the shell is directed against the at least one piercing element.

12. The lead extension of claim 10, wherein the shell is formed of a same material as the adhesive, wherein the material of the shell is at least partially cured to form the shell.

13. The lead extension of claim 10, wherein the shell is formed of a non-adhesive, solid plastic material.

14. The lead extension of claim 10, wherein the adhesive is an ultraviolet-curable adhesive.

15. The lead extension of claim 10, wherein the adhesive is a heat-curable adhesive.

16. A kit, comprising:
an implantable stimulation lead; and
the lead extension of claim 10 configured and arranged to receive a portion of the implantable stimulation lead within the connector of the lead extension.

17. The kit of claim 16, further comprising a control module coupleable to the lead extension.

18. A method of attaching a lead anchor to an electrical stimulation lead, the method comprising:
inserting a portion of the electrical stimulation lead into the lead lumen of the lead anchor of claim 1;
piercing the shell within the lead anchor to release the adhesive;
allowing the adhesive to enter the lead lumen and make contact with the lead; and
curing the adhesive.

19. The method of claim 18, wherein curing the adhesive comprises curing the adhesive with ultraviolet light.

20. The method of claim 18, wherein curing the adhesive comprises curing the adhesive with heat.

* * * * *